(12) United States Patent
Blatter et al.

(10) Patent No.: US 7,238,207 B2
(45) Date of Patent: Jul. 3, 2007

(54) SHOULDER PROSTHESIS (75) Inventors: Georges Blatter, St. Gallen (CH); Wolfgang Schwägerl, Vienna (AT); Peter Zenz, Gablitz (AT); Frank Dallmann, Schmölln (DE); Wilfried Glien, Bad Kosterlausnitz (DE); Dirk Salmon, Jonaswalde (DE); Ulrich Irlenbusch, Arnstadt (DE)

(73) Assignee: Mathys AG Bettlach (CH)

( * ) Notice: Subject to any disclaimer, the term of this patent is extended or adjusted under 35 U.S.C. 154(b) by 308 days.

(21) Appl. No.: 10/874,020

(22) Filed: Jun. 21, 2004

(65) Prior Publication Data
US 2005/0033443 A1 Feb. 10, 2005

Related U.S. Application Data (63) Continuation-in-part of application No. PCT/EP02/14634, filed on Dec. 20, 2002.

(30) Foreign Application Priority Data
Dec. 21, 2001 (DE) .......................... 201 20 703 U (51) Int. Cl.
*A61F 2/44* (2006.01)
(52) U.S. Cl. .................................. 623/17.13
(58) Field of Classification Search .. 623/19.11–19.14, 623/20.24, 22.11, 23.11, 22.42
See application file for complete search history.

(56) References Cited

U.S. PATENT DOCUMENTS

| 5,336,268 A | 8/1994 | Rispeter |
| 5,358,526 A | 10/1994 | Tornier |
| 5,800,560 A | 9/1998 | Draenert |
| 5,961,555 A | 10/1999 | Huebner |
| 6,197,062 B1 | 3/2001 | Fenlin |
| 6,206,925 B1 | 3/2001 | Tornier |
| 6,228,120 B1 * | 5/2001 | Leonard et al. .......... 623/19.12 |
| 6,736,852 B2 * | 5/2004 | Callaway et al. ........ 623/19.14 |

(Continued)

FOREIGN PATENT DOCUMENTS

DE 69221843 T2 6/1993

(Continued)

OTHER PUBLICATIONS

International Search Report- re PCT Publication #WO 2003/053280 A3, dated Aug. 19, 2003.

(Continued)

*Primary Examiner*—Alvin J. Stewart
(74) *Attorney, Agent, or Firm*—Graybeal Jackson Haley LLP (57) ABSTRACT The shoulder prosthesis has a stem (10), a ball head (20) and a middle section (30) that can be attached to the proximal end (12) of the stem (10) and to which the ball head (50) can be attached. The middle section (30) can be clamped to an attachment element (20) that is adjustable in a first direction at the proximal end (12) of the stem (10), the first direction lying in the resection plane or parallel thereto. The first direction generally runs approximately medially-laterally. The attachment element (20) can be displaceable on the stem (10) by means of a dovetail guide (15) or guided displaceable in a guide bore in the stem (10). The middle section can be clamped against the attachment element (20), whereby the attachment element (20) and the middle section (30) can be fixed.

7 Claims, 10 Drawing Sheets

U.S. PATENT DOCUMENTS

| | | | |
|---|---|---|---|
| 6,749,637 B1 * | 6/2004 | Bahler .................... | 623/19.14 |
| 6,942,699 B2 * | 9/2005 | Stone et al. ............. | 623/19.14 |
| 2001/0053935 A1 * | 12/2001 | Hartdegen et al. ....... | 623/19.12 |
| 2004/0064190 A1 * | 4/2004 | Ball et al. ................ | 623/19.14 |
| 2004/0143335 A1 * | 7/2004 | Dews et al. ............. | 623/19.14 |
| 2005/0288681 A1 * | 12/2005 | Klotz et al. ................ | 606/102 |
| 2005/0288791 A1 * | 12/2005 | Tornier et al. ........... | 623/19.13 |

FOREIGN PATENT DOCUMENTS

| | | |
|---|---|---|
| DE | G 9312218.7 | 12/1993 |
| DE | 19548154 A1 | 6/1997 |
| DE | 29918669 U1 | 2/2000 |
| DE | 19841612 A1 | 3/2000 |
| DE | 19841611 A1 | 4/2000 |
| EP | 0549480 | 6/1993 |
| EP | 0679375 A1 | 11/1995 |
| EP | 0712617 A1 | 5/1996 |
| EP | 0715836 A1 | 6/1996 |
| EP | 0953321 A1 | 11/1999 |
| FR | 2721200 | 12/1995 |
| WO | WO 01/82843 A2 | 11/2001 |

OTHER PUBLICATIONS

German Search Report—(In German language only) dated Aug. 22, 2002.

* cited by examiner

SHOULDER PROSTHESIS

CROSS-REFERENCE TO RELATED APPLICATION

This application is a continuation-in-part and claims benefit under 35 USC § 120 of PCT Application No. PCT/EP02/14634, filed 20 Dec. 2002, incorporated herein by reference, which in turn claims priority from German Patent Application No. 201 20 703.6, filed 21 Dec. 2001, incorporated herein by reference and to which priority is claimed.

BRIEF DESCRIPTION OF THE INVENTION

The invention relates to a shoulder prosthesis with a stem, with a ball head and with a middle section that can be attached to a proximal end of the stem at various positions along a first linear direction and to which the ball head can be attached.

BACKGROUND

Such a shoulder prosthesis is known from EP-A 0 953 321. The middle section has outwardly-projecting ribs by means of which it can be inserted into a recess at the proximal end of the stem in various laterally-medially staggered positions. The middle section is connected to the stem by a press fit and the ball head has a recess of constant cross-section by means of which it is fitted onto the middle section. The middle section is angled as a result of which various inclinations and retroversion angles can be set.

A shoulder prosthesis is known from U.S. Pat. No. 5,961,555 in which the middle section can be fitted onto a cone at the proximal end of the stem and the ball head is clamped by means of a conical dovetail guide. Apart from the fact that the ball head is displaced in anterior-posterior direction when clamped to the middle section, the ball head is not adjustable vis-à-vis the stem.

Shoulder prostheses in which the middle section is conically developed at both ends and can thereby be connected to the stem and the ball head are known from EP-A-0 549 480, EP-A 0 599 429, FR-A 2 721 200 and U.S. Pat. No. 6,197,062. The axes of both conical ends are angled vis-à-vis each other and/or offset vis-à-vis each other as a result of which a lateral-medial and posterior-anterior adjustment of the ball head and optionally of the retroversion angle vis-à-vis the stem is possible. A similar shoulder prosthesis is also known from DE-A 198 41 612, the middle section being disk-shaped and having axial pins, offset vis-à-vis each other, on both sides.

A shoulder prosthesis in which the middle section has a cylindrical section, the axis of which runs parallel to the stem axis and which can be clamped to the proximal end of the stem with adjustable rotation position, is known from EP-A 0 679 375. Projecting from this cylindrical section is a conical section onto which the ball head can be fitted.

Shoulder prostheses in which the middle section can be adjusted vis-à-vis the stem by means of a ball-and-socket joint, the concave surface of the ball-and-socket joint being developed in the stem, are known from EP-A 0 712 617, U.S. Pat. No. 6,228,120 and U.S. Pat. No. 6,206,925. In the case of the shoulder prosthesis known from EP-A 0 715 836, the concave surface of the ball-and-socket joint is developed in the ball head and the joint ball added at the proximal stem end.

Shoulder prostheses in which the middle section is adjustable at the proximal end of the stem in the direction of the stem axis, as a result of which the effective length of the prosthesis stem can be altered, are known from DE-A-195 48 154 and DE-U-299 18 669.

A shoulder prosthesis in which the distance between ball head and stem can be altered by providing the ball head with an axial or axis-parallel threaded section that can be screwed into a threaded bore at the proximal end of the stem is known from DE-U-93 12 218. The ball head can be fixed by means of a safety screw that can be screwed in transversely thereto.

SUMMARY OF THE INVENTION

An object of the invention is to create a shoulder prosthesis that is particularly simply constructed and in which the ball head is almost continuously adjustable vis-à-vis the stem.

This object is achieved according to an embodiment of the invention in that the middle section can be clamped to an attachment element that is adjustable in a first direction at the proximal end of the stem, the first direction lying in the resection plane or in a plane parallel thereto.

The attachment element is preferably linearly adjustable at the proximal end of the stem in a guide, preferably in medial-lateral direction, for example in a dovetail guide or a rotation-symmetrical guide. In general, the direction of adjustability lies in the resection plane or in a plane slightly parallel-displaced thereto.

The resection plane usually lies at an angle of 40° to 50° to the stem axis, i.e. the normal line of the resection plane lies at an angle of 130° to 140° to the stem axis. Joint implantations are usually carried out such that the connection surface of the implant coincides as exactly as possible with the resection surface. In the present case, the connection surface is the surface at the proximal end of the stem against which the ball head lies in the ideal case.

The middle section is preferably clamped by means of a threaded bolt that passes through a shoulder bore of the middle section and is screwed into the attachment element, as a result of which the attachment is simultaneously fixed in its guide.

Through these measures the ball head is continuously adjustable in the first direction vis-à-vis the stem. In order to make the ball head two-dimensionally adjustable vis-à-vis the stem, the middle section is preferably continuously adjustable in a second direction vis-à-vis the attachment element. The second direction runs at an angle to the first direction and is preferably approximately right-angled to the first direction.

The adjustability of the middle section vis-à-vis the attachment element can be achieved by the fact that the shoulder bore in the middle section is a slot shoulder bore pointing in anterior-posterior direction.

As a result, the ball head is continuously adjustable in two directions vis-à-vis the stem, the adjustment being intraoperative and correctable. The reproduction of inclination and retrotorsion does not take place in this case via an alignment of the ball head vis-à-vis the stem, but is achieved via resection instruments and therefore preset in the case of the shoulder prosthesis according to the invention.

In a particularly preferred design of the invention the stem has at the proximal end a connection surface which lies at an angle of approximately 40° to the stem axis and which generally coincides with the resection plane or lies at a slight distance parallel to it. The attachment element is a plug-shaped sliding block that is displaceable in a guide bore that is provided at a slight distance below the connection surface and has a proximal window in the connection surface. The sliding block has a transverse threaded bore. The middle section can be clamped against the connection surface by means of a threaded bolt that is screwed into the cross bore of the sliding block. The connection surface and the underside, lying against it, of the middle section can be serrated in order to achieve a positive-locking engagement. Instead of the serration, a roughening can also be provided. In principle any positive- and/or force-locking connection is possible.

The middle section has a slightly conical exterior and the ball head has a correspondingly conical recess, as a result of which the ball head can be connected to this by simply fitting it onto the middle section. The connection can also be achieved by positive locking, e.g. click elements, or by positive force locking, e.g. a threaded connection.

These connection means can be centred, single-eccentric or double-eccentric. In the case of a centred development, the shoulder bore of the middle section is centred relative to the exterior of the middle section and the recess or the other connection means is also provided centred in the ball head.

In the case of a single-eccentric development the shoulder bore of the middle section is centred and the conical recess or other connection means is developed eccentric in the ball head. By changing the rotation position of the ball head on the middle section the centre of the ball head can be set relative to the stem end on an orbit the radius of which equals the eccentricity. In conjunction with the setting of the middle section along the first direction a continuous adjustability of the ball head vis-à-vis the stem end in two dimensions thereby results.

It is also possible to develop the ball head centred and to provide the shoulder bore eccentrically in the middle section. In general in the case of single-eccentric development however the previous possibility is selected in which only the head ball is developed eccentric.

In the case of a double-eccentric development the shoulder bore of the middle section is arranged eccentric to the exterior of the middle section and the recess or other connection means is provided eccentric in the ball head. the double eccentricity already enables per se a continuous adjustment of the ball head vis-à-vis the stem end inside a circular area the radius of which corresponds to the sum of the two eccentricities. In addition the ball head can still be continuously adjusted in the first direction.

The stem preferably has at the proximal end one or more fins with bores for the attachment of tendons and bone fragments.

Depending on the anatomical conditions, the ball head can have a shape between a hemisphere and a very flat sphere section with an angle at centre of, for example, 90°.

The individual parts of the stem prosthesis can be produced from materials customary for endoprostheses, in particular from ceramics, titanium alloys or cobalt-chromium alloys or from unreinforced or fibre-reinforced plastic.

BRIEF DESCRIPTION OF THE DRAWINGS

Embodiments of the invention are explained in the following using the drawing. There are shown in.

DETAILED DESCRIPTION OF THE EMBODIMENTS

The shoulder prosthesis in all the embodiments consists of a stem 10, a sliding block 20 as attachment element, a middle section 30, a threaded bolt 40 and a ball head 50. The stem 10 broadens towards its proximal end 12 and ends there in a connection surface 14 that runs according to the resection plane at an angle of approximately 40° or 45° to the longitudinal axis of the stem 10.

Figure 1:
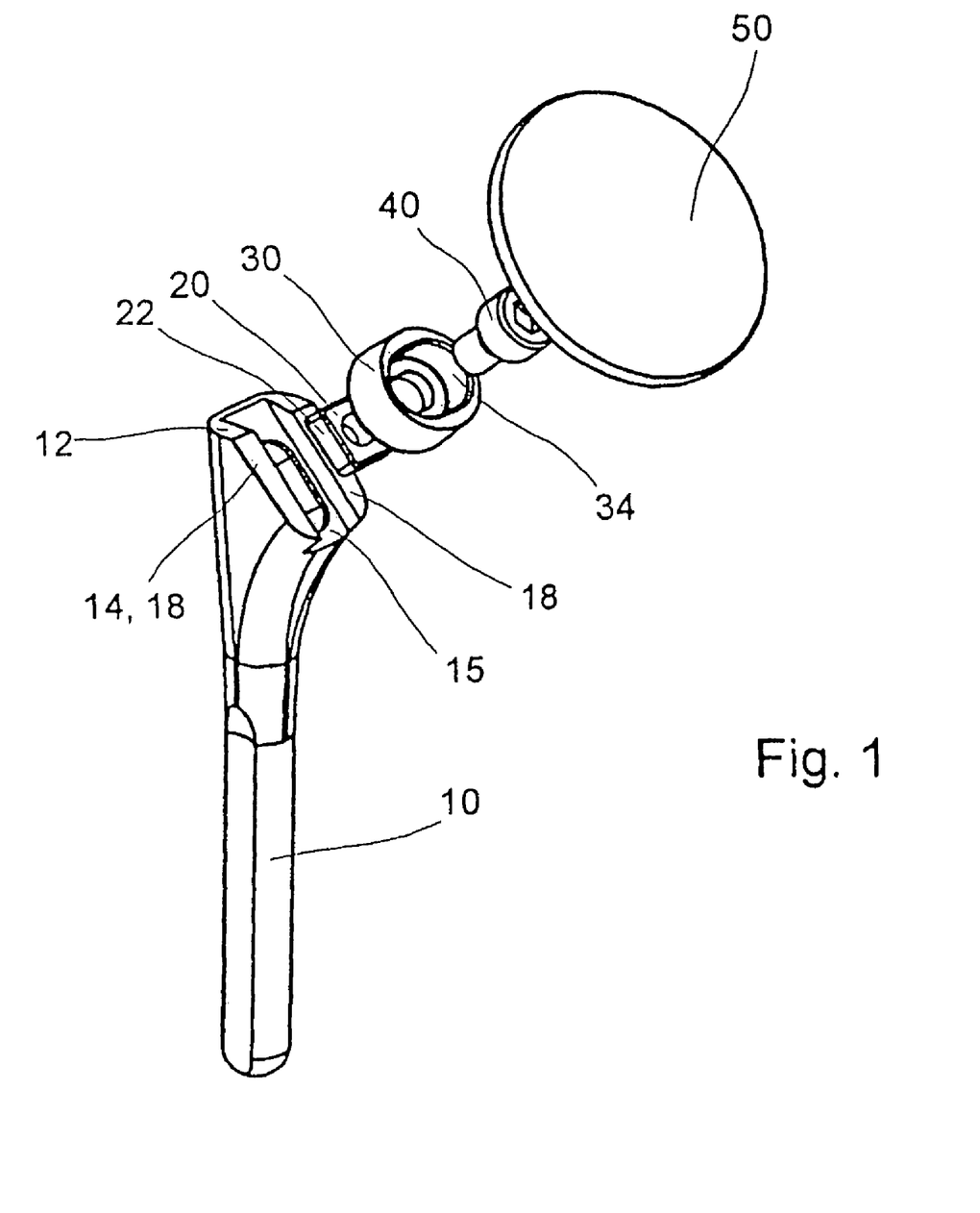
FIG. 1 shows a first embodiment of the shoulder prosthesis according to the invention in a three-dimensional exploded representation.
Figure 2:
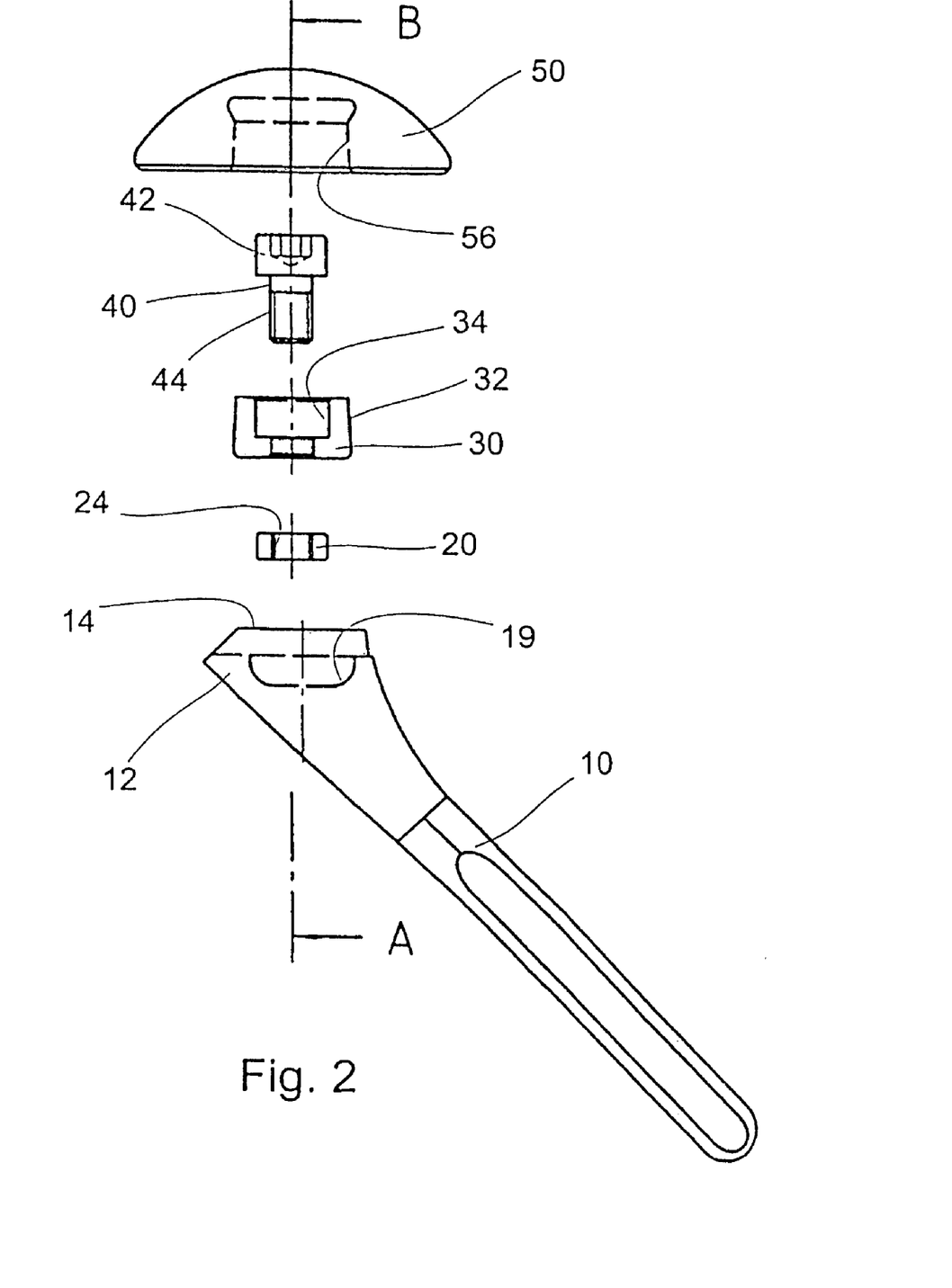
FIG. 2 is the shoulder prosthesis of FIG. 1 from the front or the rear in a disassembled representation.
Figure 3:
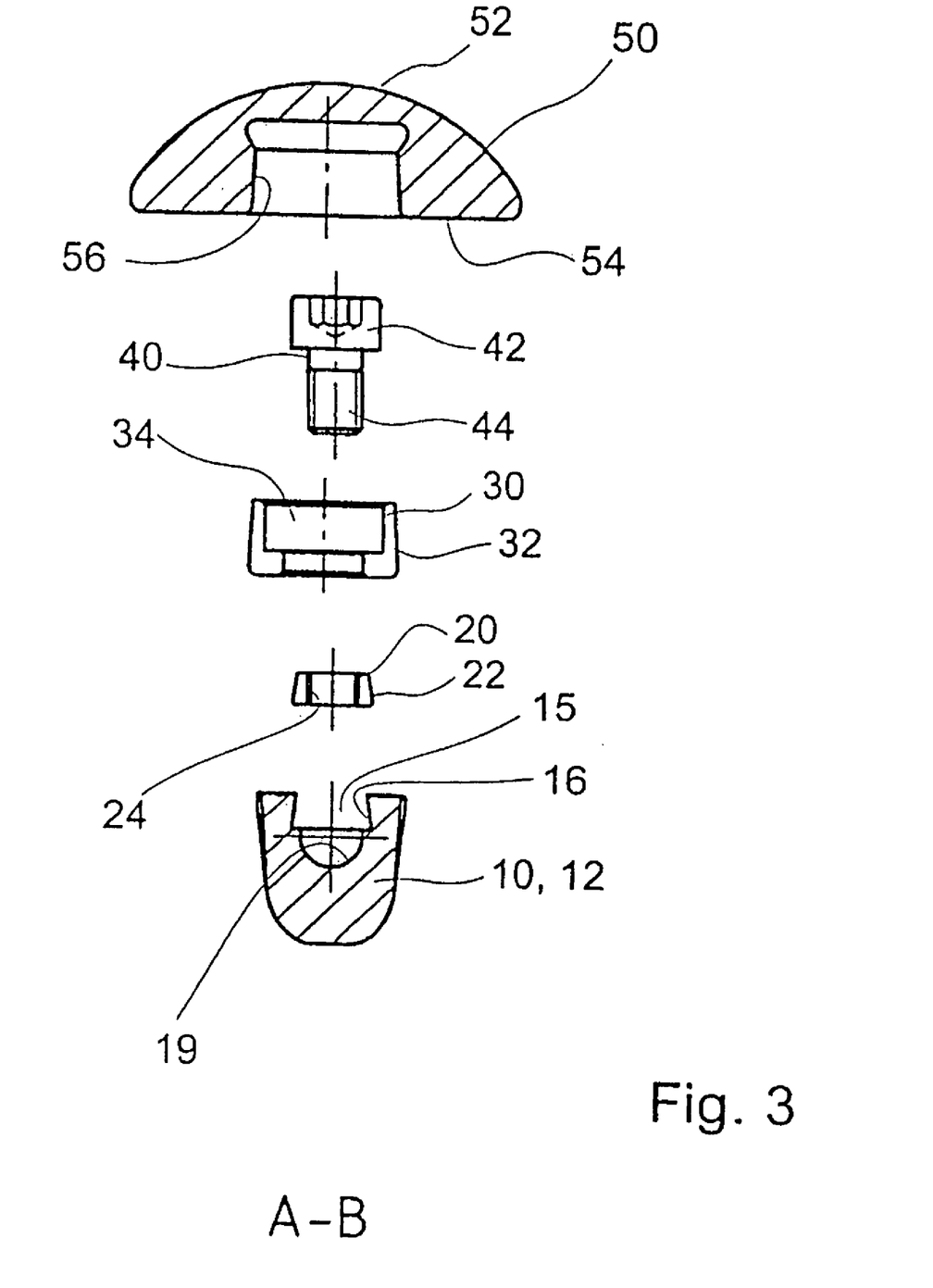
FIG. 3 is a section along A–B of FIG. 2.

In the case of the first embodiment the sliding block 20 is guided in a dovetail guide 15, to which end an inwardly-widening groove 16 is developed in the connection surface 14 and two lateral guide surfaces 22 of the overall approximately square sliding block 20 are correspondingly inclined (FIG. 3) with the result that the sliding block 20 is displaceably guided in the groove 16 in lateral-medial direction. Edges 18 stand on both sides of the groove 16 in the connection surface.

The middle section 30 has a frustum-shaped exterior 32 and an axial slot shoulder bore 34, the longer dimension of the shoulder bore 34 being directed anterior-posterior. The threaded bolt 40 is inserted into the shoulder bore 34 and screwed into a threaded bore 24 of the sliding block 20. The threaded bolt 40 has a head 42 with a hexagon socket and a threaded stem 44 and the head of the threaded bolt 40 is completely housed in the shoulder bore 34. By tightening the threaded bolt 40 the middle section 30 is clamped against the outside edges 18 of the dovetail guide 15. The end of the threaded bolt 40 extends into a recess 19 in the base of the dovetail guide 15.

Figure 4:
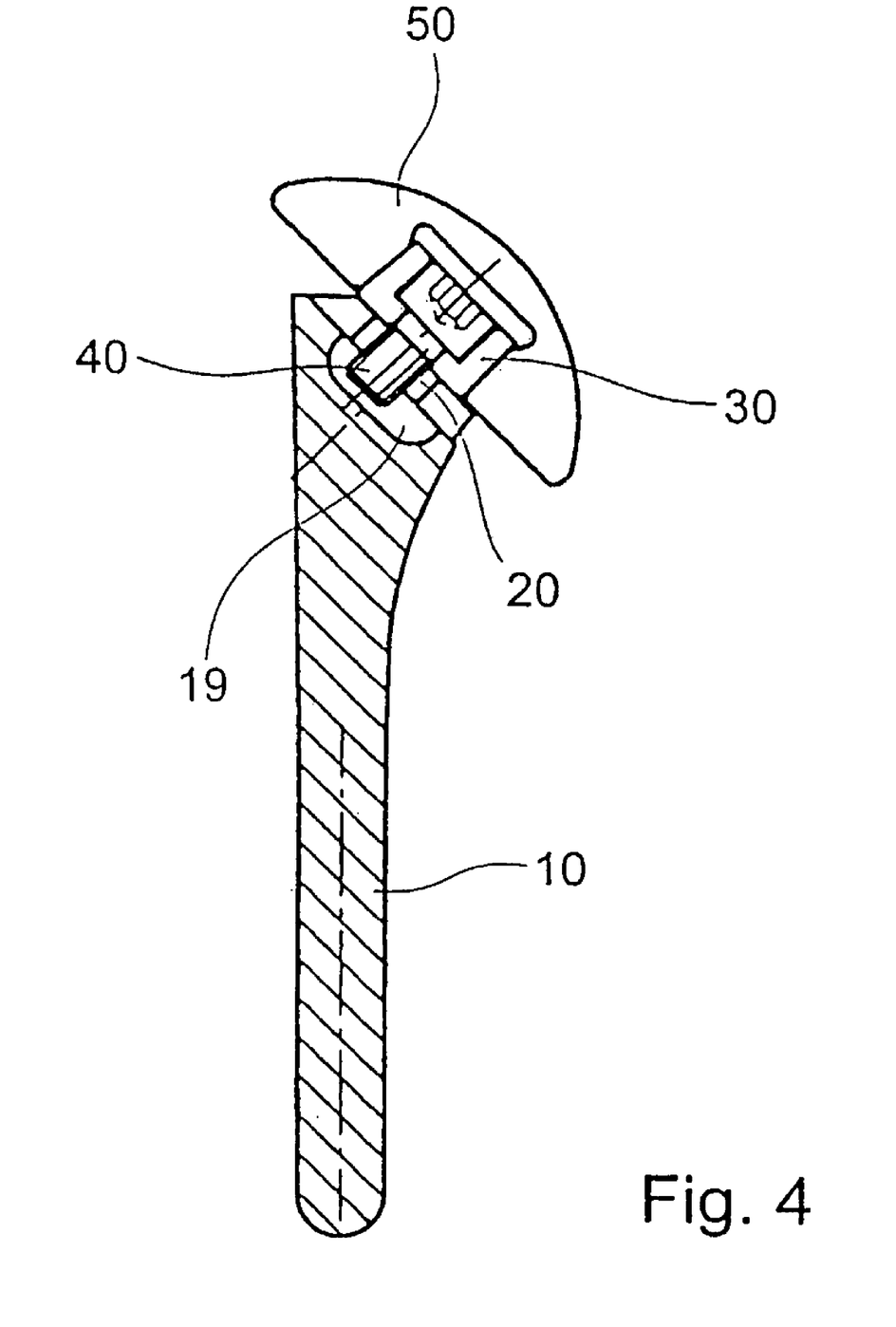
FIG. 4 shows the shoulder prosthesis of FIG. 1 in assembled state in longitudinal section.

The ball head 15 corresponds in its external shape approximately to a sphere section with an angle at centre of approximately 90°. Accordingly, it has an arched top side 52 and a level underside 54. A conically tapering recess 56 is provided in the underside 54 with the result that the ball head 50 can be fitted onto the middle section 30 with press fitting. The recess 56 is deep enough to completely house the middle section 30. As FIG. 4 shows, the underside 54 of the ball head 50, in the assembled state of the shoulder prosthesis, practically rests on the connection surface 14 and thus on the resection plane.

Figure 5:
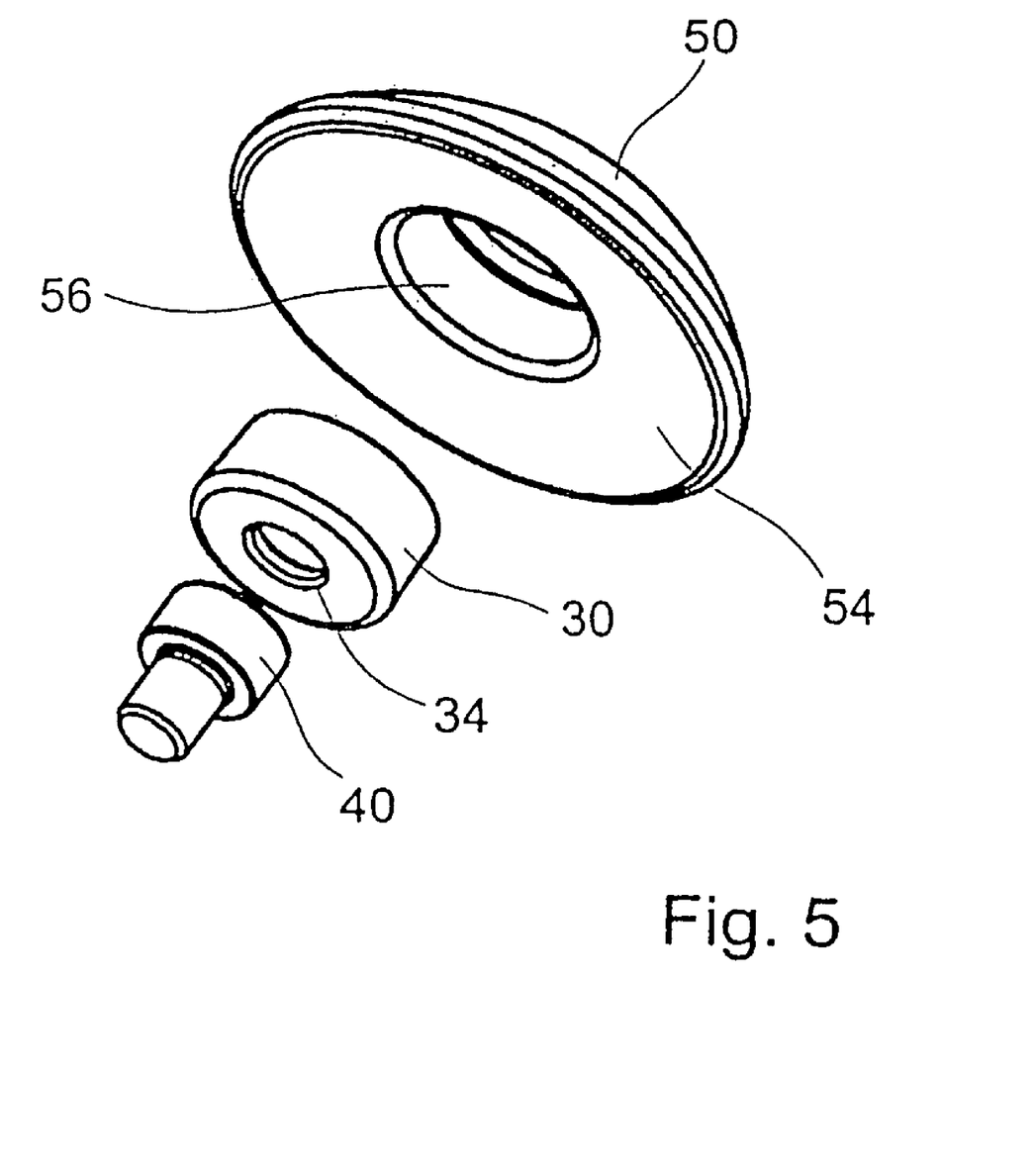
FIG. 5 is a three-dimensional representation of a centred middle section and a ball head with eccentrically arranged recess according to a second embodiment.
Figure 6:
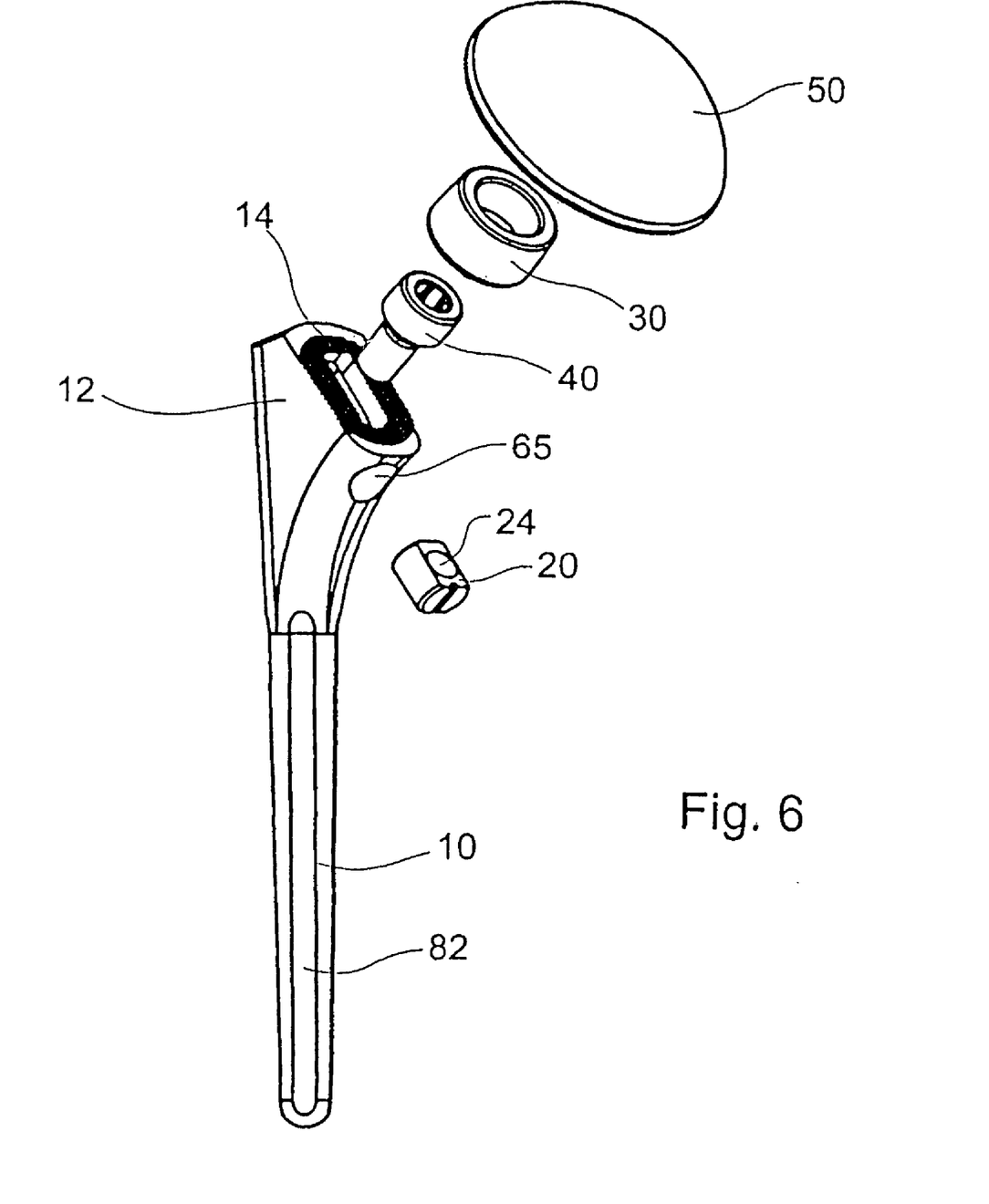
FIG. 6 illustrates a third embodiment of the shoulder prosthesis according to the invention in a three-dimensional exploded representation.
Figure 7:
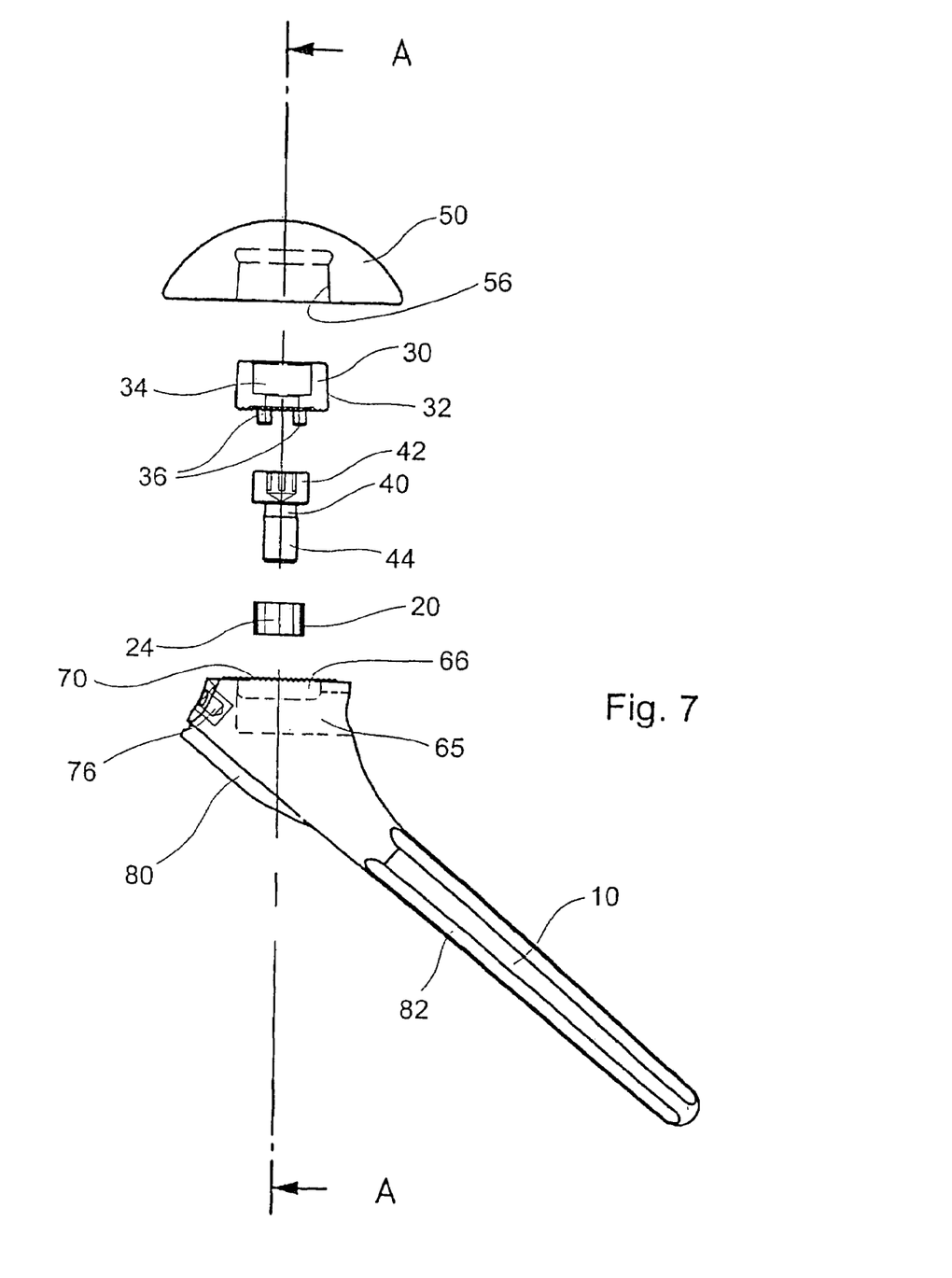
FIG. 7 shows the shoulder prosthesis of FIG. 1 from the front or the rear in a disassembled representation.
Figure 8:
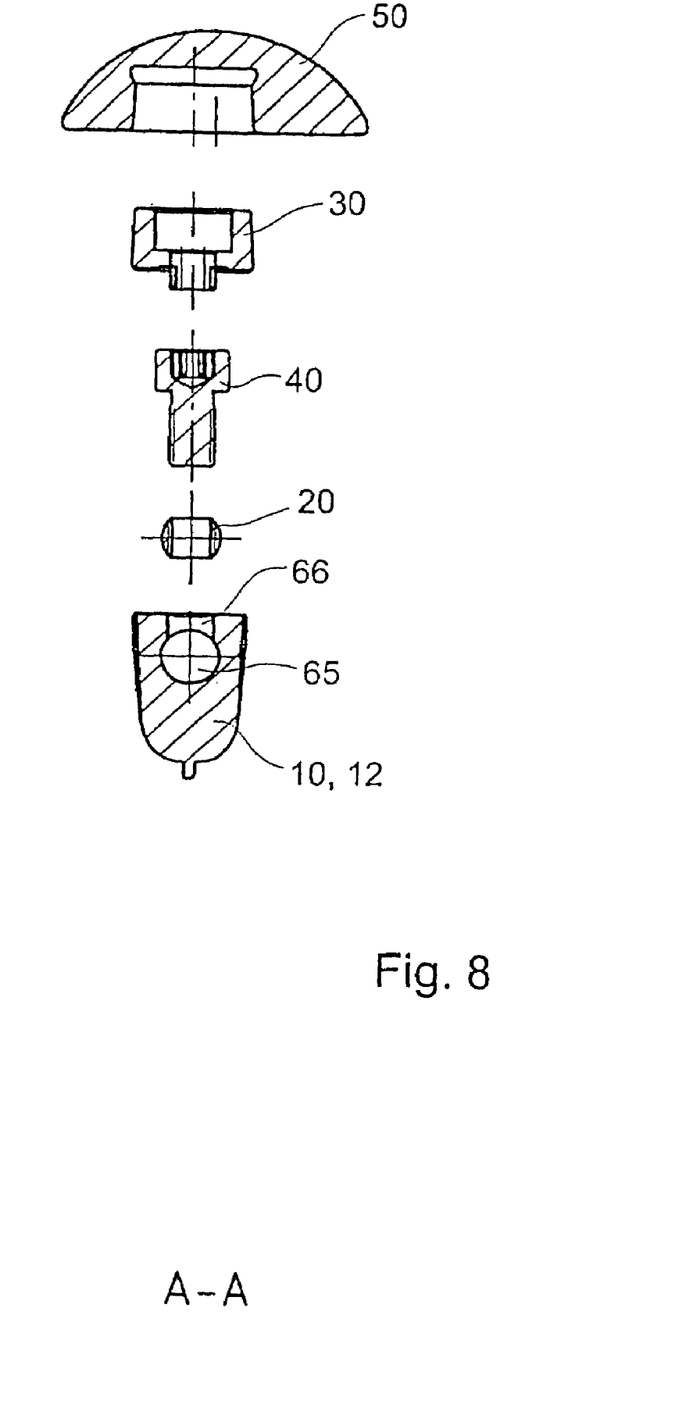
FIG. 8 is a sectional view along A—A of FIG. 7.
Figure 9:
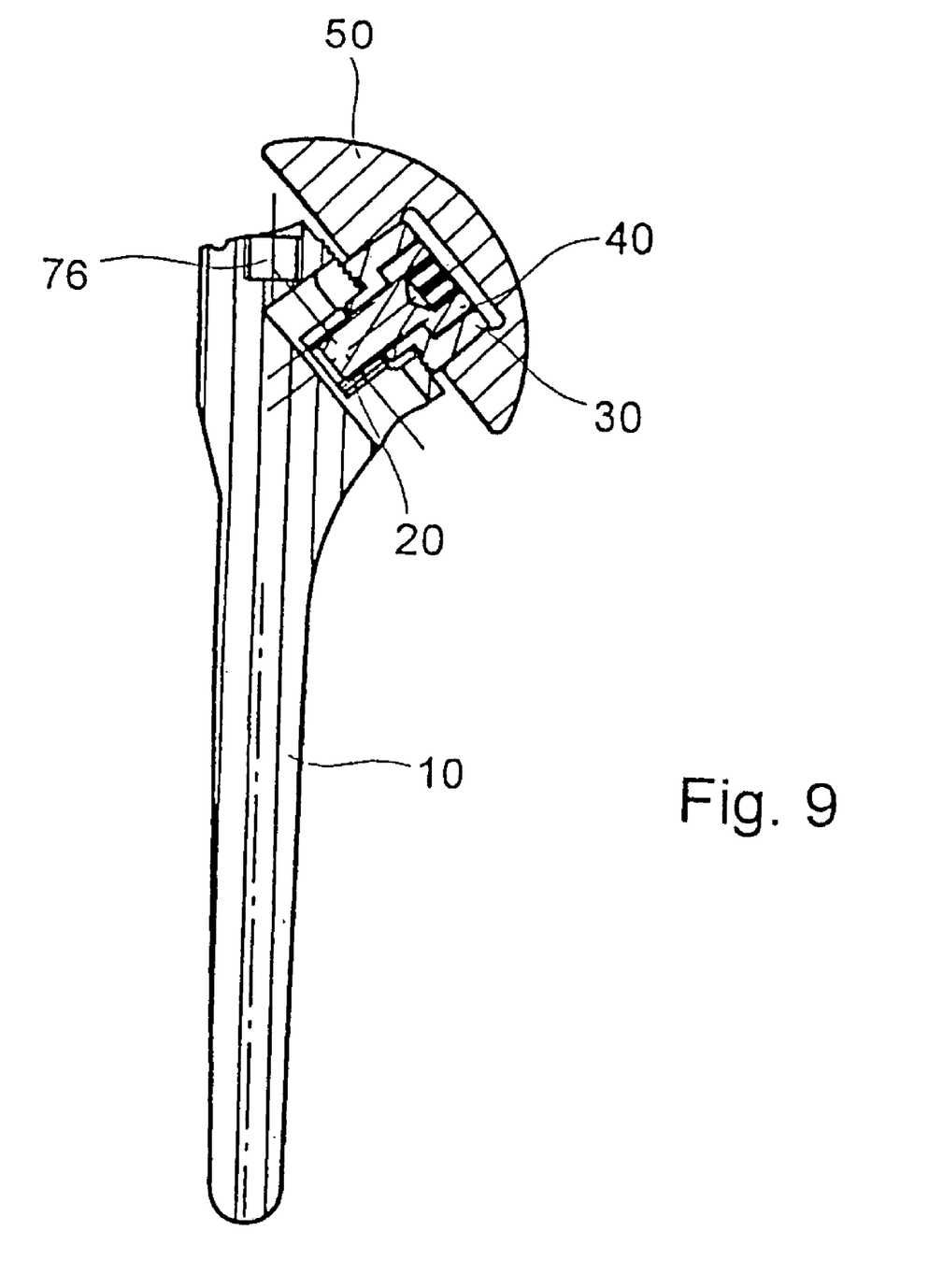
FIG. 9 shows the shoulder prosthesis of FIG. 6 in an assembled state and longitudinal section.
Figure 10:
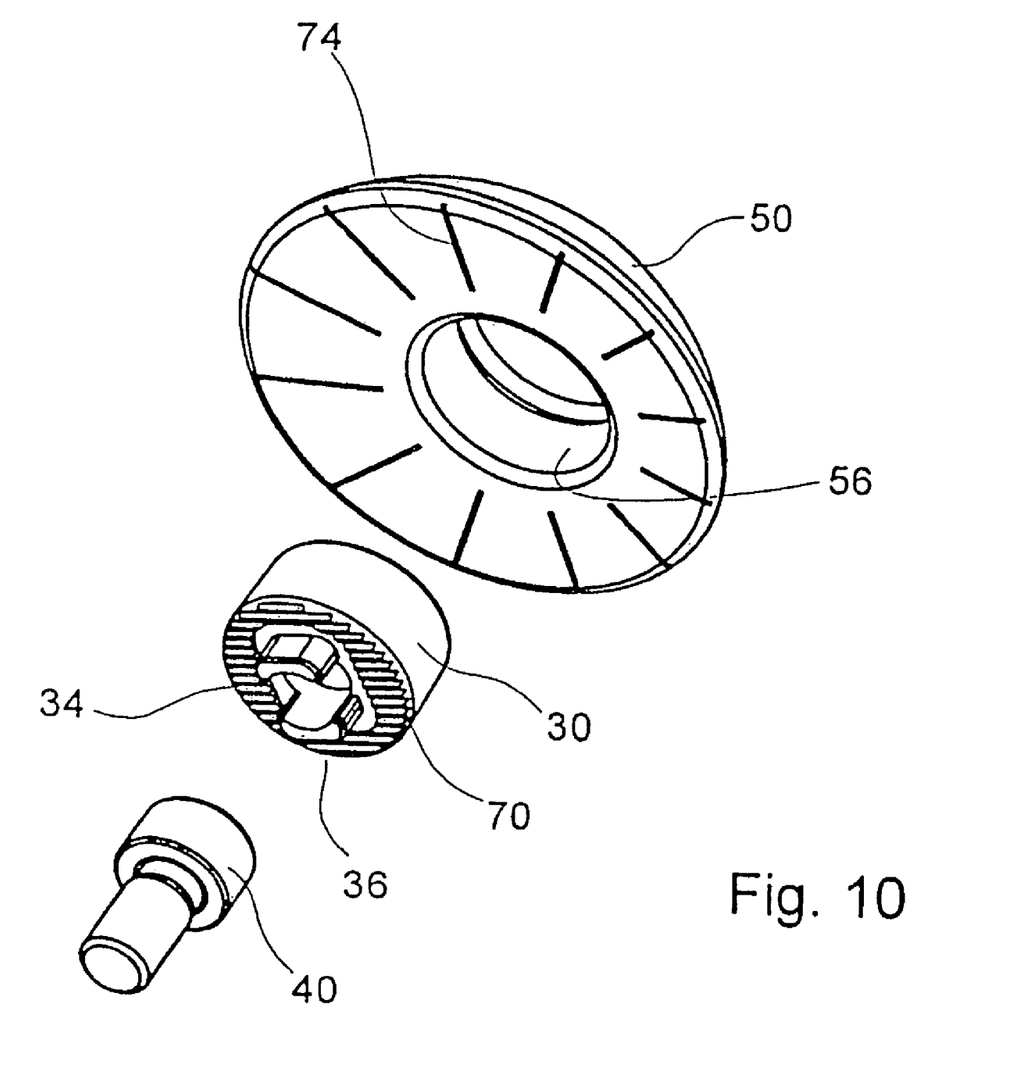
FIG. 10 is a three-dimensional representation of a centred middle section and a ball head with eccentrically arranged recess of the embodiment of FIG. 6.

FIG. 5 shows a second embodiment of a shoulder prosthesis, similar to that of FIGS. 1 to 4, the shoulder bore 34 being circular however. The middle section 30 cannot therefore be adjusted anterior-posterior. To nevertheless achieve a continuous adjustability in two dimensions, the recess 56 is arranged eccentric in the underside 54 of the ball head 50. The centre of the ball head 50 can therefore be positioned on a circular line around the longitudinal axis of the middle section 30. In conjunction with the medial-lateral adjustability of the middle section 30 at the proximal end 12 of the stem 10 a continuous adjustability is thereby likewise obtained within a surface area large enough to be able to match the anatomical conditions of the individual case.

The endoprosthesis can be assembled before or after the insertion of the stem 10 into the humeral channel, the threaded bolt 40 being loosely screwed firstly through the middle section 30 into the sliding block 20. The attachment element 20 can already be in the groove 16 at the proximal end 12 of the stem 10. On the other hand the sliding block 20 can also be inserted into the groove 16 loosely connected to the middle section 30. The stem 10 is then positioned and the middle section 30 is fixed such that the ball head 50 corresponds as closely as possible to the anatomical situation.

In the case of the third embodiment (FIGS. 6 to 10) the attachment element is a plug-shaped sliding block 20, the threaded bore 24 running transversely through the sliding block 20. The sliding block 20 is guided in a guide bore 65 in the stem 10 which is introduced from the medial position into the stem 10 and the axis of which runs parallel to the proximal connection surface 14 of the stem 10. The sliding block 20 is displaceable in the guide bore in medial-lateral direction.

A window 66 is built into the proximal connection surface 14 of the stem 10 as far as the guide bore. The threaded bolt 40 is pushed through the middle section 30 as in the first embodiment. In the case of the present third embodiment it is then guided through the window 66 and turned into the threaded bore 24 of the attachment element 20. By means of the threaded bolt 40 the middle section 30 is thereby clamped against the sliding block 20 and thus against the connection surface 14 of the stem 10. The length of the window 66 defines the medial-lateral displacement path of the middle section 30 vis-à-vis the stem 10.

The middle section 30 has a frustum-shaped exterior and a concentric through bore 34 with a blind-end bore that starts from the proximal top side or cover surface. The threaded bolt 40 is inserted, as mentioned, into the blind-end bore and inserted into the threaded bore 24 of the sliding block 20 that was previously inserted from the medial position into the guide bore 65. The threaded bolt 40 has a head with a hexagon socket and a threaded stem and the head of the screw is completely housed in the blind-end bore of the middle section 30.

A grooved structure on the connection surface 14 of the stem 10 and on the underside of the middle section 30 ensures a positive-/force-locking closure as additional security for the connection against loosening and micromovements. The grooves 70 are arranged in a 1-mm grid. Thus a defined adjustment of the ball head 50 in medial-lateral direction is ensured. There project from the underside of the middle section 30 guide lugs 36 that engage in the window 66 of the stem 10. Thus the locking and alignment of the middle section 30 relative to the stem 10 according to the groove structure is guaranteed.

The ball head 50 corresponds to that of the second embodiment. The axis of the conical recess 56 lies offset by 3 mm (eccentricity) vis-à-vis the central axis of the ball head 50. The ball head 50 is thus rotatable on a defined eccentric path about the axis of the middle section 30.

Markings 74 and inscriptions for the eccentric positions are provided on the underside of the ball head, preferably marked in twelve sections in the manner of a clock. The entrance to the guide bore 65 can be sealed by means of a seal.

Through the combination of the head eccentricity and the displacement mechanism in medial/lateral direction, any desired position of the ball head vis-à-vis the stem can thus be set on the resection plane (so-called mediodorsal offset). The adjustment ranges are ±3 mm in each case. A continuous adjustability is thus obtained within a surface area large enough to be able to match the anatomical conditions of the individual case.

The conical pitch of the middle section and head corresponds to the pitch of 1:10 used with implant cones.

A central threaded blind-end bore 76 for bracing with the setting instrument and also two blind-end bores for rotation security of the setting instrument are arranged at the proximal stem end.

The stem has proximally/laterally a fin 80 for rotation security. In the case of cement-free stem design such fins can also be provided at the anterior/posterior proximal lateral surfaces. Cement channels 82 in the distal stem region likewise serve for rotation security in the cement casing. They are rotated 4 times about the stem axis in this version.

The module comprising the stem 10, middle section 30, sliding block 20 and bolt 40 are supplied preassembled and unbraced in a sterile pack. It is also possible, if the sliding block 20 is already in the stem 10, to fit the middle section 30 with bolt 40 after implantation of the stem and to replace the middle section 30 upon inspection. In order to be able to align the sliding block 20 for the screwing-in of the bolt 40, a transverse groove 84 is cut in the end-surface of the sliding block 20.

Whereas, in the case of the embodiment of FIGS. 1 to 4, access is from the proximal/lateral position, a particular advantage of the embodiment of FIGS. 6 to 10 is that access is from the medial position. Furthermore as a result of the guide lugs 36 in connection with the grid system, a particularly reliable fixing of the middle section is achieved. The adjustment of the middle section in the embodiment of FIGS. 6 to 10 is possible not only interoperatively on the implanted stem, but also by means of a test rasp (rasp with adjustment mechanism) and external transfer of the adjustment parameters to the implant.

What is claimed is:

1. A shoulder prosthesis comprising:
   a stem having a proximal end;
   a ball head;
   a middle section, the ball head being adapted to be attached to the middle section; and
   an attachment element which is adapted to be displaced in a first direction in a guide bore in the proximal end of the stem, the first direction lying in a resection plane or in a plane parallel thereto and running approximately medially-laterally, and
   the middle section being adapted to be clamped against the attachment element through a window in the wall of the guide bore, so that the middle section can be attached to the proximal end of the stem at various positions along the first direction,
   wherein the middle section is further adapted to be adjusted in a second direction vis-à-vis the attachment element, and wherein the middle section has one of an axial slot shoulder bore, or a circular bore where the ball head has an eccentric recess arranged on an underside thereof.

2. The shoulder prosthesis according to claim 1, wherein the middle section is adapted to be connected to the attachment element through a threaded bolt and to be clamped against the proximal end of the stem.

3. The shoulder prosthesis according to claim 2, wherein the threaded bolt is guided by a slot shoulder bore in the middle section.

4. The shoulder prosthesis according to claim 1, wherein the second direction runs approximately right-angled to the first direction.

5. The shoulder prosthesis according to claim 4, wherein the second direction runs approximately anterior-posterior.

6. The shoulder prosthesis according to claim 1, wherein the ball head is eccentrically attachable to the middle section.

7. The shoulder prosthesis according to claim 1, wherein the ball head rests, in the assembled state of the endoprosthesis, with its underside practically against the proximal end of the stem.

* * * * *